US012564724B1

(12) United States Patent
Kitov

(10) Patent No.: US 12,564,724 B1
(45) Date of Patent: Mar. 3, 2026

(54) APPARATUS AND METHOD FOR MANIPULATING THE NERVOUS SYSTEM BY ELECTRIC FIELDS

(71) Applicant: Zeev Kitov, Rockville, MD (US)

(72) Inventor: Zeev Kitov, Rockville, MD (US)

( * ) Notice: Subject to any disclaimer, the term of this patent is extended or adjusted under 35 U.S.C. 154(b) by 0 days.

(21) Appl. No.: 18/822,854

(22) Filed: Sep. 3, 2024

(51) Int. Cl.
*A61N 1/40* (2006.01)

(52) U.S. Cl.
CPC ...................................... *A61N 1/40* (2013.01)

(58) Field of Classification Search
CPC ........................................................ A61N 1/40
USPC ...................................................... 607/2, 148
See application file for complete search history.

(56) References Cited

U.S. PATENT DOCUMENTS

| | | | | |
|---|---|---|---|---|
| 4,915,110 A | * | 4/1990 | Kitov ....................... | A61N 1/10 |
| | | | | 600/11 |
| 5,169,380 A | * | 12/1992 | Brennan ................... | A61N 1/40 |
| | | | | 607/45 |
| 5,782,874 A | * | 7/1998 | Loos ................... | A61N 1/36025 |
| | | | | 607/2 |
| 7,228,178 B2 | * | 6/2007 | Carroll ............... | A61N 1/36025 |
| | | | | 607/45 |

* cited by examiner

*Primary Examiner* — Mark W. Bockelman
(74) *Attorney, Agent, or Firm* — Barry Choobin; Patent 360

(57) ABSTRACT

Apparatus and method for affecting the subject's neural system by applying an Electric Field generated by an electrode system floating with respect to the skin surface of the subject for achieving neurologic effects, such as analgesia, muscle relaxation, stress control, etc. The architecture of the electrode system generates an enhanced Electric Field in conditions of limited voltages applied to limited-size electrodes. Administering the electric fields to some selected or predetermined spots on the subject's body results in specific and reproducible effects.

16 Claims, 8 Drawing Sheets

Fig. 2
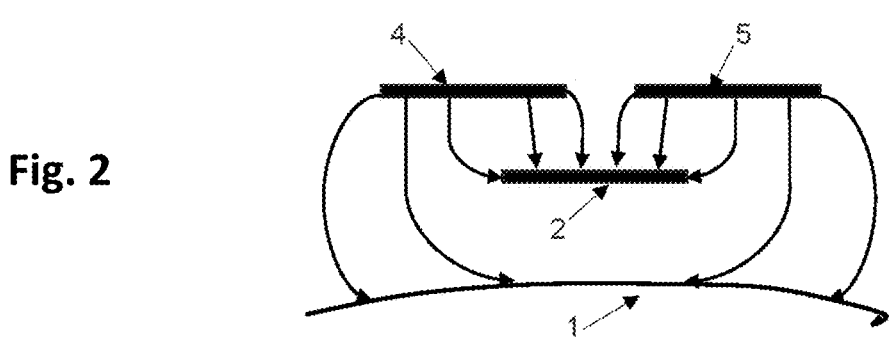
Fig. 3
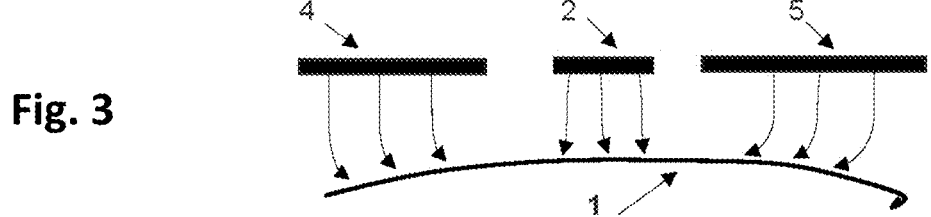
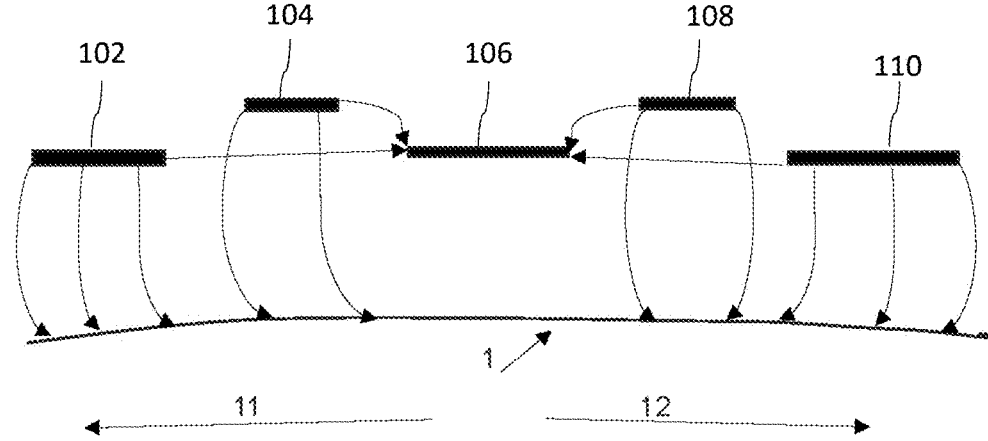
Fig. 4

Fig. 11A                          Fig. 11B

APPARATUS AND METHOD FOR MANIPULATING THE NERVOUS SYSTEM BY ELECTRIC FIELDS

FIELD OF INVENTION

The present invention relates to an apparatus and method for manipulating the nervous system by the electric field, and more particularly, the present invention relates to an apparatus and method for administering exogenous electric fields to the skin for manipulating the nervous system.

BACKGROUND

Nervous system stimulation through exogenous electric fields is well-known in art. Typically, in the conventional methods for exogenous administration of electric fields, the electrodes are isolated from the subject's body, so the only plausible factor affecting the subject is the electric field generated by the electrodes. The nervous stimulation by these devices has been used with certain degrees of success in anesthesia, relaxation, and sleep, as well as for treating pain, intractable epilepsy, behavioral disorders, movement disorders, and cardiac arrhythmia. These devices have several advantages over electro-contact stimulation, and the primary advantage is that there is no need for high-quality contacts for the subject skin, which is a nuisance.

The U.S. Pat. No. 4,915,110 granted to Theri Teck Inc. teaches a pair of electrodes separated from the subject body by an insulator. An oscillator provides electrical pulses to the electrodes resulting in the formation of external or fringe EF that is applied to selected spots on the body. The device showed results comparable to non-invasive acupuncture in analgesia, muscle relaxation, and stress control.

Another U.S. Pat. No. 5,169,380 granted to Brennan teaches a device to enhance sleep. The device has a pair of electrodes that can be positioned on the left and right side of a subject's head; each electrode is insulated from the head. The electrodes are supplied with a voltage with a frequency of about 5 and 40 cycles per second with a peak-to-peak value of about 100 V.

Another U.S. Pat. No. 5,782,874 granted to Hendricus G. Loos teaches a structure of coplanar electrodes and a pair of electrodes arranged in a capacitor-like structure to form a fringe field. The device is intended for use in general relaxation, sexual excitement, and sleep. The disclosure teaches that the device can treat medical conditions, such as tremors, seizures, panic attacks, and many neurological disorders. The patent further discusses a theoretical foundation for applying low-frequency and low-intensity EF to affect the peripheral neural system.

Conventional devices rely on fringe EF generated by a capacitor-like electrode structure that induces currents or charges in the subject's skin. The electrode structure is separated from the subject's skin by an air gap, which has a huge resistance and negligible capacitance (some picofarads) through which the voltage and current are induced. Also, the epidermis has a substantial capacitance of about 1 uF per square centimeter. Therefore, this air gap and the epidermis form a capacitive divider, reducing the voltage of the device electrodes to a value applied to the skin by a factor of $10^9$-$10^{12}$ times. As a result, the currents induced into the skin tissue are in levels of about pico-amperes per square centimeter and voltages in nanovolts.

In conventional devices, the currents induced into the subject's body are too small to cause classic nerve stimulation by the neural membrane polarization effect. Any therapeutic effect can be due to the stochastic modulation of spontaneous subthreshold waves in neurons affecting the neural synaptic activity. Therefore, any therapeutic effects depend on the size of the stimulated skin area. For example, the skin area to be stimulated for therapeutic effect can range up to 600 cm². To cover such a huge skin area, substantially large electrodes must be used, and the electrodes must be placed farther from the skin area. This severely limits the portability of such devices, and the results are often unsatisfactory. When the stimulated area is too large, the specificity of the obtained effects might be lost.

Thus, it may be desirable to have a system that requires a smaller skin area to be stimulated without affecting the efficacy of electrostimulation. There is a need to improve the efficacy of electrostimulation devices.

SUMMARY OF THE INVENTION

The following presents a simplified summary of one or more embodiments of the present invention to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of this invention is to mitigate the disadvantages of conventional systems and methods for electric field application.

It is an object of this invention that electric fields generated by limited voltage signals can be applied to small areas of the body for the desired therapeutic effect.

Another object of this invention is to use smaller electrodes to induce charges and currents in the skin.

In one aspect, disclosed are an apparatus and method for generating electric fields that can interact with a subject's body by inducing charges and currents in the skin tissues, without any electric contact with the skin or body, providing desired neurological effects.

In one aspect, disclosed is an apparatus that includes a signal source and electrode system that can receive signals from the signal source for generating EF. The signal source can be an oscillator or DC power source. The electrode system forms internal EFs between adjacent surfaces of electrodes and external EFs between opposite surfaces of the same electrodes extending beyond the electrode system perimeter and forming so-called fringe fields. Adjacent or internal surfaces of different plane electrodes are surfaces facing each other with the angle between them ranging from 0° to 90°. The opposite surfaces of the same plane electrodes have angles between them ranging from 90° to 360°.

The internal and external fields are complementary; they arise simultaneously between two electrodes carrying different potentials. When the angle between two electrodes is 90° the internal electric field occurs in the space between 0° and 90° and the external or fringe field occurs in the space between 90° and 360°. Any electric field extending beyond the perimeter of the interelectrode space may be called an "external or fringe" field and another complementary field that is limited by the interelectrode space is then called the internal field. The external field reaches the skin surface.

The electrode system of the device may include multiple reference and active electrodes, making the generation of multiple Electric fields possible. Theoretically speaking, the Electric Field may be formed between each active electrode and each reference electrode, as well as between each pair of the active electrodes and each pair of the reference electrodes. In practice, however, some of these fields may be neglected. However, in general, the apparatus may generate an Electric Field composed of multiple spatially and temporally joined Electric fields of individual pairs of electrodes. It is like a case when different wires are coupled to the same load and carry different signals to this load. In this particular case, different pairs of electrodes form different fields carrying different signals to the same target, the skin surface. It may be considered as the summation or joining of transmitted EF signals directed to the skin. The external EFs interact with the body tissues, particularly with the epidermis and dermis layers of the skin inducing charges and currents, which produce neurological effects.

In one aspect, disclosed is an apparatus that includes a hand-held device having at least two electrodes separated by dielectric matter which can be air or any suitable dielectric material; the EF is electrically floating with respect to the skin surface. When a voltage signal is applied to the electrodes, they form two EFs: an internal field between adjacent surfaces of the electrodes and an external field between outside surfaces of the electrodes (fringe field); the latter field being formed outside of the electrode's perimeter, reaches and affects the tissues of the subject skin. The AC electrical fringe field is pulsating with the same frequency as the internal AC field since both are generated by the same signal source.

The disclosed apparatus includes a novel electrode system, which is more efficient in exogenous induction of currents in the skin tissue of the subject. The enhancement of the induced currents is achieved either (1) by an increase in the total length of the electrode edges, or (2) by the formation of highly curvilinear EF lines having substantial value of the second spatial derivative.

Besides that, to maximize the effect, the electrode device can be applied not only to local spots in afflicted zones of the body, but also to their associated zones, and to general functional centers, which mostly coincide with known acupuncture points.

BRIEF DESCRIPTION OF DRAWINGS

The accompanying figures, which are incorporated herein, form part of the specification and illustrate embodiments of the present invention. Together with the description, the figures further explain the principles of the present invention and enable a person skilled in the relevant arts to make and use the invention.

FIG. 2 is a top view of the orthographic projection of the non-coplanar electrode system as in FIG. 1A, according to an exemplary embodiment of the present invention.

FIG. 3 is a top view of the orthographic projection of the coplanar electrode system as in FIG. 1B, according to an exemplary embodiment of the present invention.

FIG. 4 is a top view of the orthographic projection of the integrated electrode system of the apparatus, according to an exemplary embodiment of the present invention.

FIG. 11A shows an A-shape electrode structure, FIG. 11B shows a V-shape electrode structure.

DETAILED DESCRIPTION

Figure 1A:
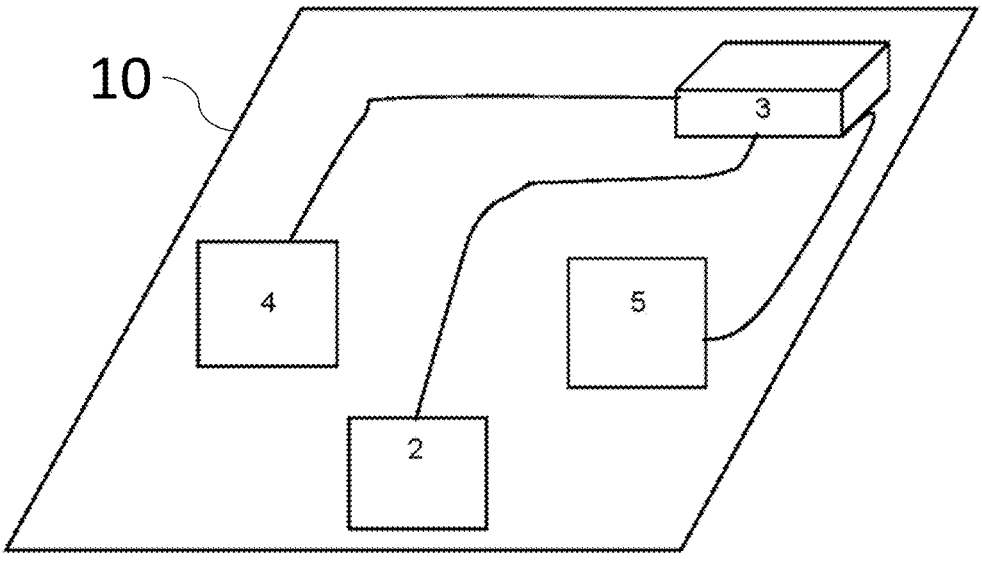
FIG. 1A is a block diagram showing the non-coplanar electrode system and FIG. 1B is a block diagram showing the coplanar electrode system, according to an exemplary embodiment of the present invention.

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is to describe particular embodiments only and is not intended to be limiting to embodiments of the invention. As used herein, the singular forms "a", "an" and "the" are intended to include the plural forms as well, unless the context clearly indicates otherwise. It will be further understood that the terms "comprise", "comprising,", "includes" and/or "including" when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely to illustrate the general principles of the invention since the scope of the invention will be best defined by the allowed claims of any resulting patent.

The invention will now be described in connection with certain preferred embodiments with reference to the following illustrative figures so that it may be better understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Definitions

Neuromodulation: neuromodulation is a stochastic modulation of spontaneous subthreshold waves in neurons, which may affect a normal over-threshold neural synaptic activity. Such modulation may affect the activity of a target organ or somatic functional system.

Electrode: The electrode may be formed of a conductive plate, a conductive wire including conductive wiring grid and pins, and some terminals of electronic parts.

Reference Electrodes: Reference electrodes are the electrodes electrically coupled to the reference potential of the power supply source. The reference potential may be zero voltage of the power supply source, a maximum voltage of the power supply source, or any other stabilized value of voltage. The reference electrodes implement screening and focusing of the EFs formed by the potential difference between the active electrode(s) and the reference electrode(s). The reference electrodes may be formed as conductive plates, wires including wiring grids and pins, and some terminals of electronic parts Active electrodes: The active electrodes are the electrodes electrically coupled to the signal wire carrying active signals generated by the signal source, which may be AC signals, DC signals, or a combination thereof, e.g., DC-biased AC signals. The active electrodes may be formed as conductive plates, wires including wiring grids and pins, and some terminals of electronic parts.

Front edge of the printed circuit board: The front edge of the printed circuit board or PCB is the edge, which is positioned in parallel with one of the insulating walls of the enclosure, the latter is used as a means of attachment to the skin and when the device is in use is positioned in parallel with the tangent to the skin surface. Therefore, when the device is in use, the front edge of the device PCB is positioned in parallel with the tangent of the skin surface.

Device PCB: the device PCB is the main PCB carrying electronic parts and electrodes.

Electrode PCB: The electrode PCB is another PCB in which an insulative sheet serves as the dielectric and the conductive plates are formed either by a continuous copper clad or by the pattern of etched copper clad.

Coplanar electrode system: the term coplanar electrode system defines a group of electrodes in which the group members, such as conductive plates, wires including wiring grids, or terminals of electronic parts are positioned in the same plane with the other electrode(s). As to dipole electronic parts, their positioning is determined according to their dominant axis, e.g., the straight line between dipole terminals.

Non-coplanar electrode system: The term non-coplanar electrode system defines a group of electrodes in which the group members, e.g. conductive plates, wiring grids, or dipole electronic parts are positioned in different planes.

Each area on one side of the human body has its symmetrical associated area on the other side of the body (back side vs. front side and right side vs. left side) located at about the same height.

Dermatome: The dermatome is an area on the body that relies on a specific spinal nerve. They may become painful due to "referred pain", e.g., when some internal organ coupled to the same nerve experiences some problem.

The described invention pertains to an apparatus and method for exogenous application of electric fields to the skin, without the electrodes contacting the skin, for neuromodulation. The apparatus includes a signal source and an electrode system for generating the electric field according to the present invention. The electrode system includes reference electrodes and active electrodes. The reference electrodes are the electrodes coupled to the reference wiring of a power source, such that the reference electrode receives DC potential equal to the minimal voltage of the power source, the maximum value voltage of the power source, or any other stabilized value of voltage. The active electrodes are the electrodes coupled to the signal wiring carrying the active signals generated by the signal source, which may be DC signals, AC signals, or a combination thereof, e.g., DC-biased AC signals.

In certain implementations, the electrodes can be implemented in the form of conductive plates, wire grids, or terminals of electronic parts. Examples of the electronic parts include resistors, capacitors, rectifying diodes, Zener diodes, and LED's. Also, the electronic parts may include the ICs incorporating the above-recited parts.

In certain implementations, electrodes can be positioned either in a coplanar or non-coplanar way, which depends on their mutual positioning, either in a single plane or in different planes.

Figure 1B:
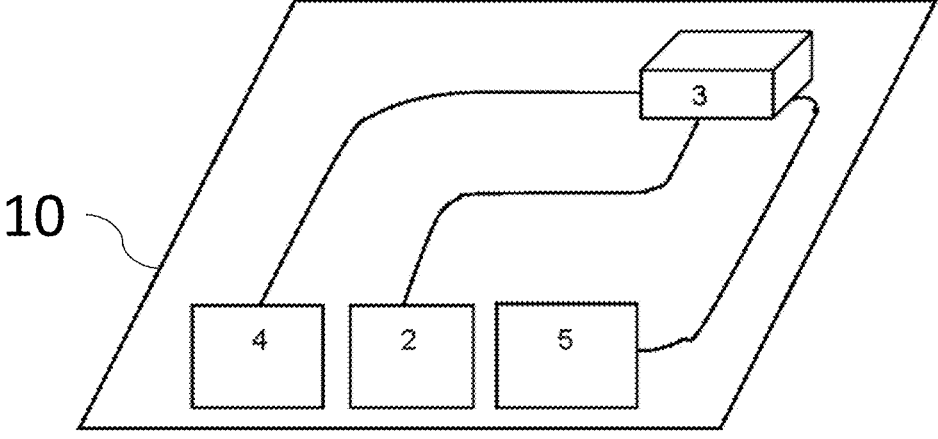

Referring to FIGS. 1A and 1B show the electrode system mounted on a printed circuit board 10. The electrode system includes a reference electrode 2 which is in the form of a conducting plate. The reference electrode can be coupled to a reference terminal of a signal source 3. The electrode system includes two active electrodes i.e., a first active electrode 4 and a second active electrode 5. As shown in FIG. 1A, the active electrodes 4 and 5 are spatially positioned behind the reference electrode. The active electrodes can be coupled to the outputs of the signal source via signal-carrying connective PCB traces. The signals generated by the signal source and supplied to the active electrodes may have different shapes. The signal source may generate some value of DC potential, or a time-varying signal, or their combination, e.g., DC-biased AC signal.

Due to the potential difference between the active electrode plates 4 and 5 and the reference electrode plate 2, the EF lines are being formed between them, as shown by curved vector lines in FIG. 2. Additional field lines, called fringe electric lines, indicated by curved vector lines, are formed between the active electrodes 4, 5 and a subject skin surface 1, as shown in FIG. 2, which shows the top orthographic projection of the electrode structure of FIG. 1A. The fringe EF lines interact with the skin layers inducing some amount of charge in the epidermis and dermis of the skin, thus facilitating neurologic effects.

When the active electrodes are mounted on a common PC board together with the reference electrode, in a parallel way, but at some vertical distance from the reference electrode, the whole electrode structure becomes three-dimensional. Positioning of the electrodes on the PC board allows easy fixation of their mutual positions.

Signal sources may be implemented in the form of any electronic means supplying either AC time-varying signals, DC potential signals, or combinations thereof, e.g. DC DC-biased AC signals.

In FIG. 1A the active electrodes 4 and 5 are shown positioned in a three-dimensional way, e.g., being in parallel with the reference electrode, but at some vertical distance from the reference electrode. Another way of positioning is shown in FIG. 1B, wherein the active electrodes are set in a coplanar way with the reference electrode, e.g. the reference electrode and the active electrodes are set in the same plane. In such a structure, the fringe capacitance and therefore the fringe field are both maximized as shown in FIG. 3.

FIGS. 2-4 show top views of orthographic projections of the coplanar and non-coplanar electrode systems of the apparatus. FIG. 2 presents the top orthographic view of the non-coplanar system shown in FIG. 1A, FIG. 3 presents the top orthographic view of the coplanar system shown in FIG. 1B, and FIG. 4 presents the top orthographic view of the integrated electrode system, described below.

FIG. 2 presents a three-dimensional electrode pattern forming the EF such that it is concentrated in between the plates and only a few percent of the lines (fringe lines) extended to the subject skin 1. However, as shown in FIG. 3, the coplanar electrode system forms the EF such that a substantial part of the EF extends beyond the perimeter of the electrode structure and interacts with the skin of the subject. Since the bottom under-electrode space in FIG. 3 structure has larger fringe (external) capacitance than that of FIG. 2, wherein only edges of plates 4 and 5 provide field lines reaching the skin, the FIG. 3 structure demonstrates higher efficacy. Under equal conditions, it can induce larger currents and charges into the subject skin. However, in certain implementations, the non-coplanar EF form shown in FIG. 2 may be preferable.

Figure 6:
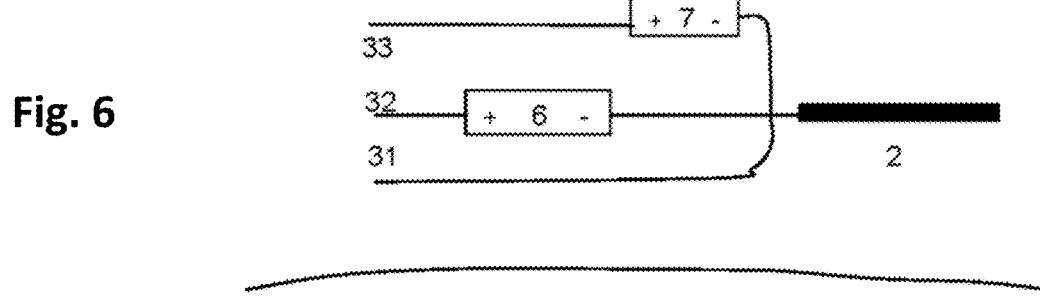
FIG. 6 is a schematic diagram of the integrated electrode system of the apparatus, according to an exemplary embodiment of the present invention.

As indicated in FIG. 6, different active electrodes may receive different signals from signal sources, via lines 32 and 33 with respect to the reference wire line 31. The active signals may differ in frequency, shape, or phase. For example, an EF with frequency f1 is supplied to the active electrode 6 with respect to the common reference electrode 2, while another EF with frequency f2 is being supplied to another active electrode 7 with respect to the common reference electrode 2. EFs of these frequencies f1 and f2 are formed between Electrodes 6 and 7 and the reference electrode 2. As a result, two different frequency signals will be injected together into the skin. In other words, the electrode systems with multiple active electrodes, as shown in FIGS. 1-4, 6, 7, and 10, allow the summation of signals induced into the skin by different active electrodes. Besides that, the recited signals may be just DC potentials, AC signals, or DC-biased AC signals. Such combining of the EF signals from different electrodes may be viewed as a spatial and temporal summation of different Electric fields.

In practice, both types of electrode architecture i.e., coplanar and non-coplanar, may be combined in a single integrated structure. FIG. 4 shows multiple active electrode structures, including electrodes 102 and 110 coplanar with reference electrode 106. It further includes electrodes 104 and 108 non-coplanar with the reference electrode 106. All active electrodes are being coupled to the signal source outputs carrying some potential different from the reference potential. Therefore, EF lines are formed between the conductive plates of each active electrode and reference electrode. As shown in FIG. 4, the skin area 1 underlying the reference electrode 106 receives about the same values of EF, so there is almost no lateral gradient in EF intensity and practically negligible induced potentials, while the other areas underlying active electrodes are subjected to lateral gradients of EFs projections onto the skin surface and causing a flow of radial currents 11 and 12 between area underlying electrode 106 and its periphery.

However, to ensure the proper functioning of such a structure, some additional measures should be taken. The active electrodes 102 and 110 in the coplanar plate should be located at some lateral distance from the reference electrode 106 leaving some gap between them to prevent screening or distortion of the EF lines of active non-coplanar electrodes 104 and 108 by the reference electrode 106 and coplanar active electrodes 102 and 110, which may block fringe lines of electrodes 104 and 108, and prevent them from extending beyond perimeter of the electrode structure and contacting the subject skin surface.

Figure 5:
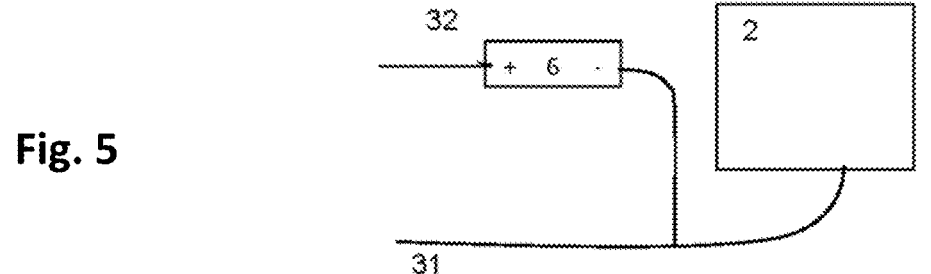
FIG. 5 is a schematic diagram of the electrode system with a capacitor part used as an active electrode, according to an exemplary embodiment of the present invention.

FIG. 5 and FIG. 6 show different versions of positioning and connections of the active electrodes with respect to the reference electrode 2. In FIG. 5, the capacitor active electrode 6 is positioned in a coplanar way with the reference plate electrode 2. FIG. 6 shows two capacitor active electrodes 6 and 7, electrode 6 is positioned in a coplanar way, and electrode 7 is in the non-one coplanar way with respect to the reference electrode 2.

Figure 7:
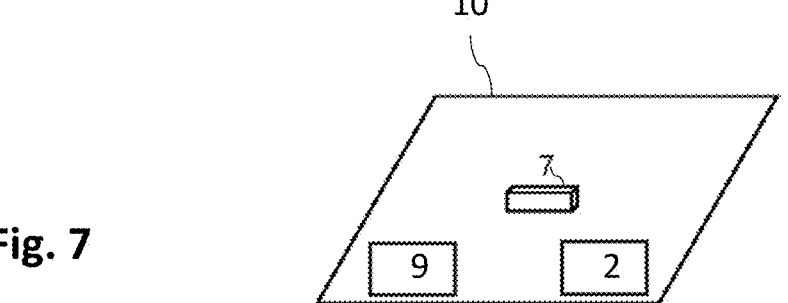
FIG. 7 shows the focusing positioning of the reference electrodes, according to an exemplary embodiment of the present invention.

FIG. 7 shows the electrode structure, adjusted for focusing the fringe electric field. Here two coplanar reference electrodes 2 and 9 in the form of conductive plates are positioned vertically in the vicinity and parallel to the front edge of the device PCB. They are separated by some gap. Additionally, active electrode 7, such as the capacitor, is positioned at some distance from the reference electrodes and aligned to the gap. In such an arrangement of electrodes, part of the fringe electric field can pass through the gap to the target.

Now regarding enhancement of the currents induced into the skin of the subject. As well-known in the art, values of longitudinal currents induced into the biological matter are proportional to the second-order longitudinal derivative of the EF strength. Therefore, in the case of plate electrodes having conductive surfaces in parallel with the skin surface 1 (FIG. 8A), only edges of the electrodes actively participate in inducing the currents (since their ellipsoid shape Electric lines are significantly curvilinear thus having noticeable second derivatives), while most of the electrode area does not produce a noticeable effect since the EF lines are almost straight lines, which are only slightly curvilinear, thus hardly producing any noticeable first derivative and practically zero second derivative. In other words, for efficiently inducing some amount of current into the tissue, the applied EF strength should be as much as possible curvilinear across the skin target area.

Figures 8A, 8B, 9, 10:
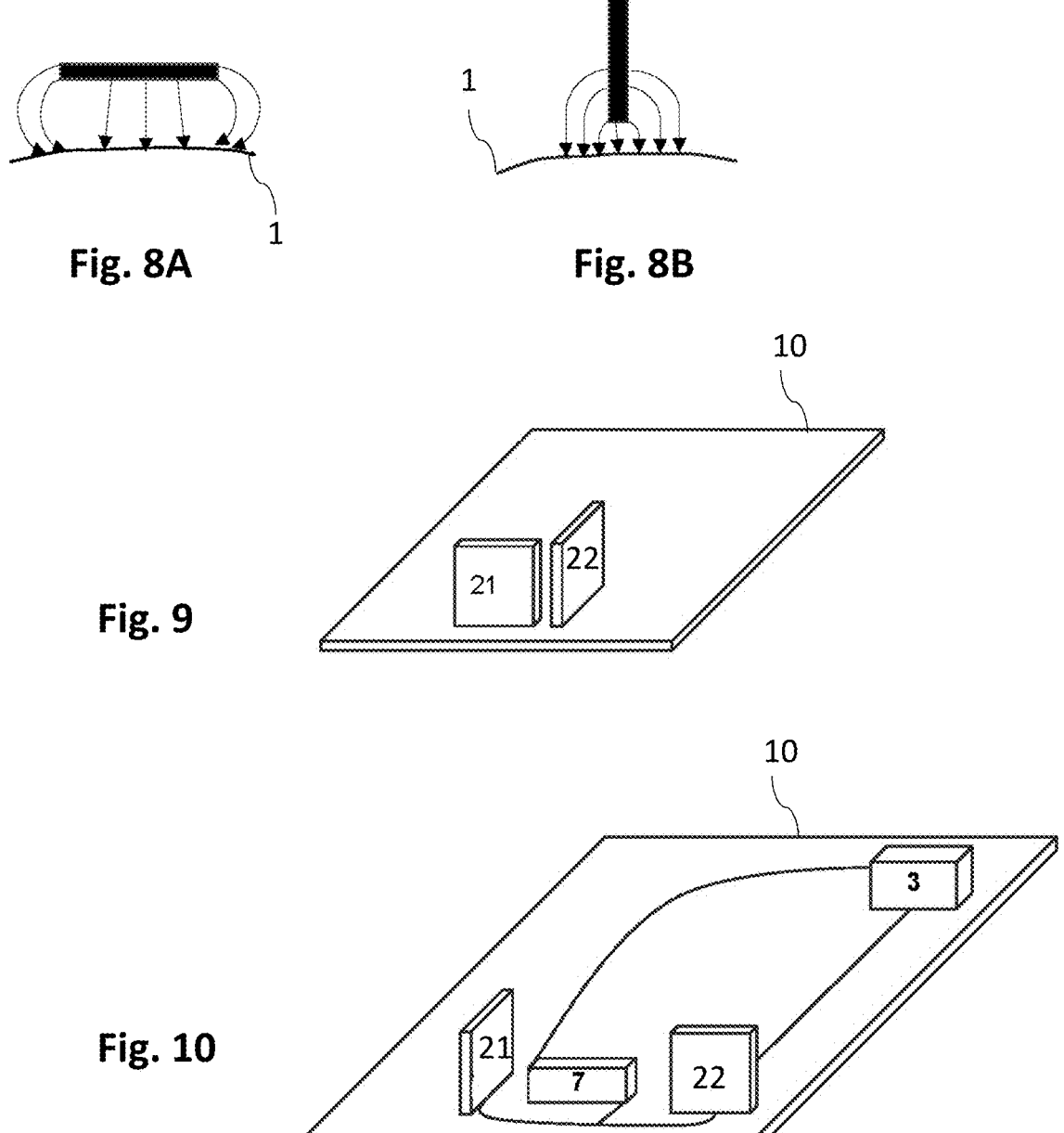
FIG. 8A shows parallel positioning of plate electrodes with respect to the skin surface and FIG. 8B shows perpendicular or vertical positioning of the plate electrodes with respect to the skin surface, according to an exemplary embodiment of the present invention.
FIG. 9 shows the electrode structure combining the parallel and the vertical electrodes, according to an exemplary embodiment of the present invention.
FIG. 10 shows a multiple-electrode structure with two reference electrodes and coplanar active electrodes, according to an exemplary embodiment of the present invention.

Such considerations resulted in another electrode form shown in FIG. 8B, wherein the conductive surface of the plate electrode is oriented orthogonally or vertically with respect to the skin surface 1 tangent line. In such a case, as shown, a smaller skin area underneath the electrode would receive a higher value of induced currents than under the parallel-oriented electrode. This is because most of the EF lines have strong curvilinear shapes and therefore substantial gradient components.

A comparison of FIGS. 8A and 8B shows that the EF under vertically oriented electrode 8B covers a small area, but the lines of the EF have a strong curvilinear shape, thus being able to induce a relatively high current into the skin tissue. At the same time, the EF under parallel oriented electrode 8A covers a large area, but most of the EF lines have a shape close to direct lines across the active area of the skin, thus inducing small or even negligible current values into the skin tissue. In the case of FIG. 8A only the electrode edges provide curved shape lines, which may induce some current values into the skin.

The definition of stimulation stands for the raising of levels of physiological or nervous activity in the body. Sedation stands for the calming or abatement of neural and/or mental overactivity. These terms are used for the description of effects obtained by the application of parallel or vertically positioned electrodes. In this sense, the electrode structure of FIG. 8A causes stimulation, while the electrode structure of FIG. 8B brings sedation.

FIG. 9 shows the electrode structure combining the electrodes arranged perpendicularly to each other. The electrode structure of FIG. 9 is a combination of FIG. 8A and FIG. 8B electrodes. Here the first electrode 21 is attached vertically to the surface of device board 10 with its own surface in parallel with the front (bottom) edge of the PCB and therefore to the skin of the subject. The second electrode 22 is also attached vertically to the surface of the device board with its own surface perpendicular to the front edge of the device PCB, and therefore, to the skin of the subject skin.

The electrode 21 may be set as the reference electrode. When electrode 22 is coupled to the signal source and used as an active electrode, the strong and laterally gradient EF is formed. Such an EF has the highest concentration in the interelectrode gap and gradually subsides along the surfaces of both the reference electrode 21 and the active electrode 22. Several vertical electrodes, like electrode 22 may be added to the electrode structure; for example, four electrodes, with one vertical electrode to each side of the square shape electrode 21, or six electrodes, with one vertical electrode to each side of the hexagon shape horizontal electrode. The active electrode 22 interacts with the reference horizontal electrode 21 via the interelectrode gap, forming a highly curvilinear EF line. In such a formation, the fringe field between the electrodes would have a curved form with strong second derivatives. It should be noted that this electrode structure is formed according to the enhanced curvature concept.

In all discussed structures the reference electrodes perform a focusing function forming the shape of external or fringe EFs contacting the skin surface of the subject. However, as shown in FIG. 8, the shapes of the EFs also depend on the way of positioning of the reference electrodes. The vertical reference electrode 21 would focus the EF with a strong Electric charge in a limited area of the skin, while the parallel reference electrode 22 would focus the field projection in a wider area with a smaller value of the charge.

FIG. 10 shows multiple electrode structures including two reference electrodes 21 and 22 located in the vicinity of the front edge of the PCB. The first reference electrode 21 is mounted vertically with respect to the PCB front edge, while the second reference electrode 22 is mounted in parallel with the front edge of the PCB. As shown, both reference electrodes are being coupled to the signal source reference potential. The active electrode 7 is a capacitor with one or both terminals used as electrodes. The capacitor is mounted in the vicinity of the front edge of the PCB in between the reference electrodes. The capacitor active electrode is coupled to the signal output of the signal source. It may receive one of the following signals: AC signal, DC signal, or AC-biased signal. Due to the potential difference between the active electrode 7 and each of the reference electrodes 21 and 22, two EFs were formed: interelectrode EF between electrodes 7 and 21 and another EF between electrodes 7 and 22 due to the potential difference between the active electrode 7, and reference electrodes. The reference electrodes play the role of focusing and forming the resulting field shape and intensity. The field near the bottom edge of reference electrode 21 will have a sharply focused projection on the skin with the enhanced value of induced current, while the field under the bottom surface of another reference electrode 22 will be a larger spot with a lower value of induced current. These features of the electrode system have been discussed above in describing FIG. 8.

Figure 11C:
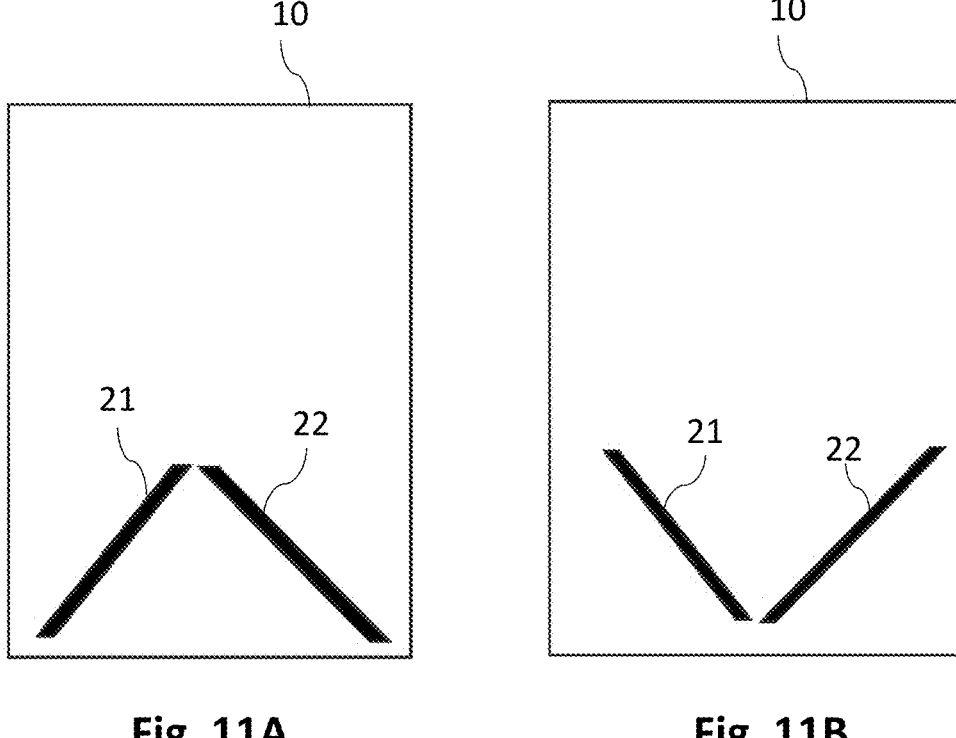
FIG. 11C shows a capacitor-like electrode structure, according to an exemplary embodiment of the present invention.
Figure 11C:
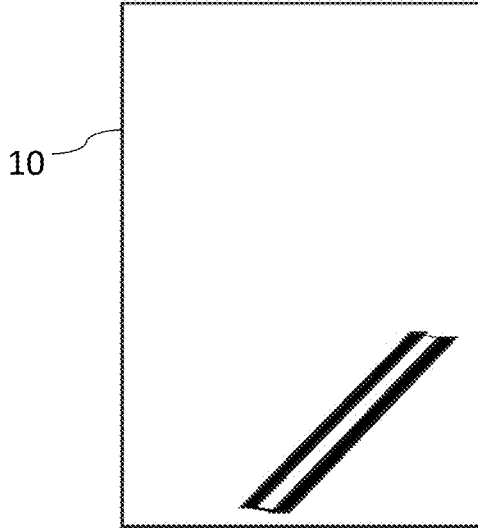

FIG. 9 electrode structure may be modified, as shown in FIGS. 11A-11C, presenting the view from the top. FIG. 11A shows the reference, and the active electrodes are implemented as conductive plates, attached vertically on the top of the PCB surface, and arranged at an angle of 45° with respect to the front edge of the PCB, such that their proximal or adjacent edges separated by a narrow gap set at a larger distance from the front edge of the PCB than their distal (remote) edges. This structure is labeled as an A-shape.

Alternatively, as shown in FIG. 11B, the reference, and the active electrodes may be implemented as conductive plates, positioned on the top of the PCB surface, and arranged at an angle of 45° with respect to the front edge of the PCB, such that their proximal or adjacent edges of the plates separated by a narrow gap set closer to the front edge of the PCB than their distal (remote) edges. This structure is labeled as a V-shape.

Finally, FIG. 11C shows the reference and the active electrodes arranged in the form of a capacitor-like structure, wherein the conductive plates indicated by black color lines are separated by dielectric, while a whole structure is positioned at the angle of 45° with respect to the front edge of the PCB and the front wall of the device. Actually, the capacitor-like electrode structure may be formed by using another PCB or electrode PCB; in such structure, the electrode PCB insulative sheet serves as the dielectric, and the electrode conductive plates are formed by a copper clad.

As to electrode structure shown in FIG. 12, it was stated above, that for efficient induction of the current into the tissue, the applied EF lines should have a strongly curvilinear form across an active area. In the case of plate electrodes having conductive surfaces in parallel with the skin surface, as shown in FIG. 8A, only the edges of the electrodes actively participate in inducing the currents because of their ellipsoid shape. The electric lines have noticeable second derivatives and produce a noticeable amount of tissue current. At the same time, most of the electrode area does not produce a noticeable effect, since the EF lines are almost straight lines, which are only slightly curvilinear, thus hardly producing any noticeable first derivative and next to zero second derivative.

Figure 12A:
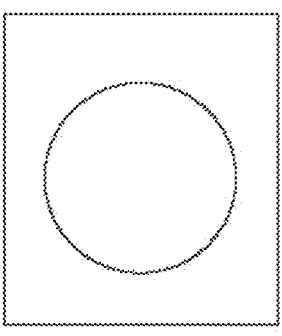
FIG. 12A shows a single-hole solution for increasing the total edge length of an electrode.
Figure 12B:
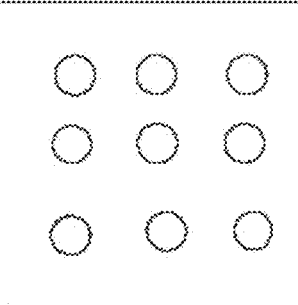
FIG. 12B shows a multiple hole's solution for increasing the total edge length of an electrode.
Figure 12C:
FIG. 12C is a cross-sectional view of a double-sided copper-clad PCB with through holes, according to an exemplary embodiment of the present invention.

FIGS. 12A-12C shows two solutions for enhancing the electrode efficacy by increasing the entire edge length. As shown in FIG. 12A, in addition to the conductive plate edges a circular hole cut through the plate. As is clear, the circumference of the hole provides an additional edge lengthy line, which results in an increase of the entire line forming curvilinear lines and consequently in the increased amount of induced current. Yet another solution for the same problem is shown in FIG. 12B, wherein multiple holes were made in the conductive plate. Each of the holes contributes to an increase of the total edge length forming curvilinear EF lines and enhancing the total value of the induced current. Both electrode structures shown in FIGS. 12A and 12B may be manufactured in the form of a copper-clad covering PCB with drilled holes. FIG. 12C shows a cross-sectional view of a double-sided copper-clad PCB with two drilled holes. The horizontal copper clads are shown in black color and two vertical through holes are shown as running through the PCB layer. When one side of copper clad is coupled to the reference potential and another one to the active signal, the obtained structure becomes a highly efficient current-induc-ing electrode structure. Drilled holes provide edges on both sides of the PCB. Due to the proximity between copper-clad layers both the internal and fringe fields become strong, while the fringe EFs of the holes due to their curvilinearity contribute to the total value of induced current.

Figure 13A:
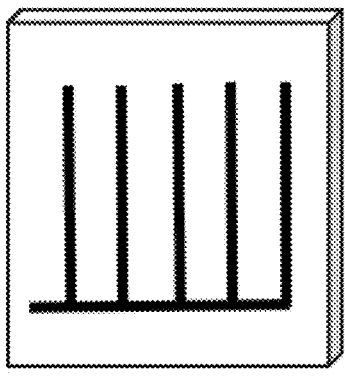
FIGS. 13A and 13B show the electrodes in the form of non-coplanar wire grids printed on two sides of PCB, according to an exemplary embodiment of the present invention.
Figure 13B:
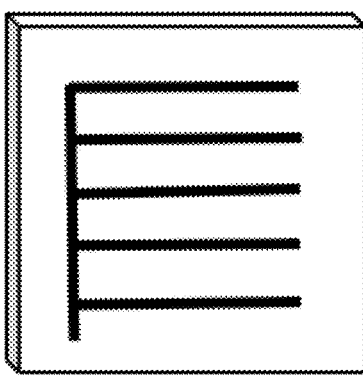

Additionally, the wiring grid electrode structure may be implemented as shown in FIGS. 13A and 13B, wherein it is formed by two non-coplanar spatially parallel sets of wires separated by an insulator. Both wiring sets are implemented as a set of conductive traces printed on different sides of a common PCB. FIG. 13A shows the front side of the PCB, and FIG. 13B the back side of the PCB. The traces on the sides of the PCB are mutually orthogonal or perpendicular. The front side wiring is coupled to the reference potential, thus making the reference side of the PCB, while the back side is coupled to the active signal of the signal source and is used as an active side of the PCB. Sharp point-like EFs are formed in the points of intersection of projections of two grids. Accordingly, the fringe field of the electrode system is highly curvilinear inducing the enhanced value of current into the tissue. This PCB with electrode structure may be used being positioned either vertically to the skin surface when the front edge of the PCB, which is for example, the bottom side, is turned to the skin, or it may be positioned in parallel with the skin surface, such that the reference side of the PCB is turned to the skin. The presented structure may be used as a power supply wiring for the assembly of the board electronic circuit.

As stated above, the active signal may have any form of signal including an AC series of pulses, but alternatively, it may be a fixed DC potential provided by the power source. In the latter case, the wiring grid electrodes may be imple-mented by the power supply wiring of the device, wherein one wiring grid, for example, FIG. 13A, carries the reference potential and the other one, for example, FIG. 13B carries the power supply voltage. In such a case, the PCB of the device may be such that the printed PCB traces of the power supply lines of the device are being used not only for supplying the power to ICs and other parts of the device but at the same time being forming an EF electrode structure.

In such case, if the number of branches in the power supply wiring grids of the device is not sufficient for enhancing enough the efficacy of the electrode system, new additional traces may be coupled to both the reference and the active wiring grid.

Figure 14A:
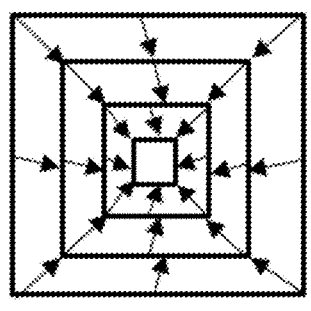
FIG. 14A shows a top view of a pyramidal electrode structure.
Figure 14B:
FIG. 14B shows a side view of the pyramidal electrode structure.
Figure 14C:
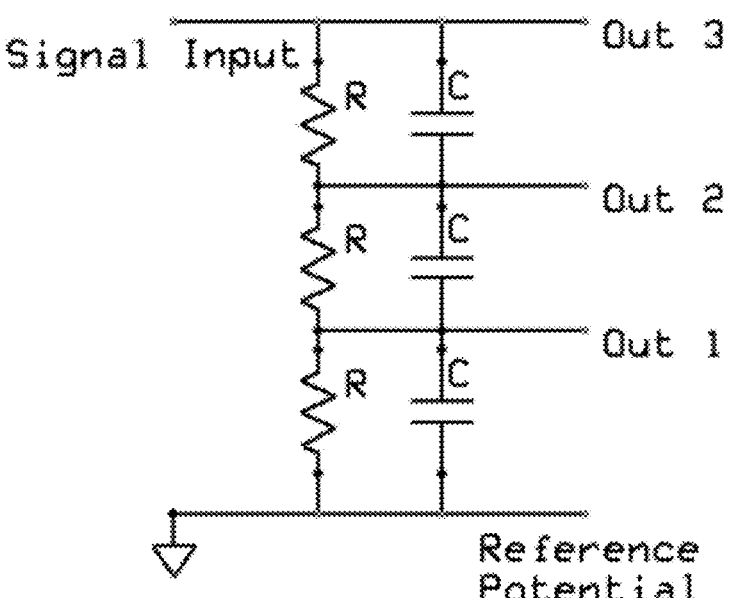
FIG. 14C shows a schematic view of multistage voltage divider supplying signals to active electrodes.
Figure 14D:
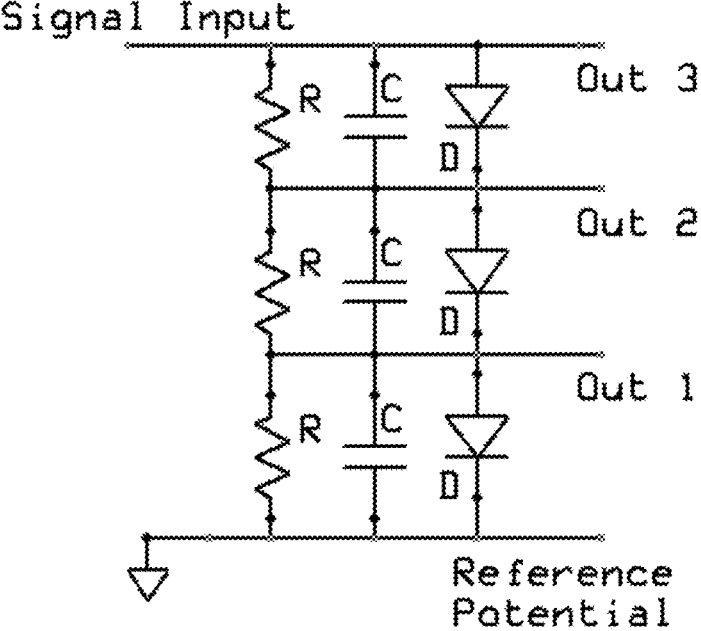
FIG. 14D shows a schematic view of the voltage divider with fixed value outputs, according to an exemplary embodiment of the present invention.

Yet another electrode structure is shown in FIGS. 14A and 14B. This structure is called a pyramid electrode and includes multiple layers. Each layer incorporates an equi-lateral conductive plate marked black, as shown in FIG. 14B, and an insulative layer with a matching size marked white. FIG. 14A shows a top view of the structure including equilateral conductive polygon plates having for example 4 sides, however, any other polygon shape, such as hexagon, octagon, and even circular shape is possible. Starting from the bottom layer each consequent layer has a smaller size than the preceding layer and the top layer may have an extremely small area. This pyramid electrode structure is coupled to the signal source via the signal adjustment circuit, which is a multi-stage voltage divider (FIG. 14C). Each conductive plate of the electrode is coupled to one of the nodes between two adjacent divider stages. Each stage of the voltage divider includes a parallel coupled resistor and capacitor, and optionally the diode (FIG. 14D), which ensures a specific value of the voltage of about 0.5 V, which is the voltage drop across the conducting diode. As a result, the signal adjustment circuit reduces the signal potential such that the conductive plates receive the signal of the same shape with an amplitude gradually reducing from the largest layer to the smallest layer. Let us take for example the second layer, which has two adjacent conductive plates, one plate of its own size since it is a part of the second layer, and another one of smaller size, which is part of the third layer. These conductive plates have different potentials; the second layer conductive plate has a potential higher than the third conductive plate. In a multilayer pyramid such an arrange-ment is repeated multiple times. The largest layer conductive plate has the highest potential, while the smallest conductive layer has the smallest potential. As a result, an EF pattern including multiple EF lines between adjacent edges, as shown in FIG. 14A, is obtained. Due to a voltage difference between adjacent conductive edges, every couple of adja-cent edges produces along its entire surface a cluster of EF lines directed from the periphery to the center on the top of the pyramid. As a result, in such an electrode system, the curvilinear EF line of the edges, as shown in FIG. 14A, occupies a substantial part of the electrode area, and as a result, it may induce a higher value of current into the skin tissue than a single couple of the reference plus active electrodes.

One practical way to produce the pyramid electrode structure would be by replacing each layer with a printed circuit board or PCB. In such a structure the printed circuit board would play both roles; the insulative layer would be replaced with fiberglass matter of the board and the con-ductive layer would be replaced with a thin copper clad printed on the board surface.

For practical use, this electrode structure should be set in position when the pyramid height is vertical to the subject skin, or in other words, the smallest size layer should face the subject skin. When the RC divider is used as the signal-adjusting circuit (FIG. 14C), any shape of the active signal, either AC or steady DC voltage may be applied. When the diodes are integrated into the divider stages (FIG. 14D), such adjusting circuits may preferably be used with a steady DC voltage signal. Both electrode systems of FIG. 12B and FIG. 14 are based on the same concept of enhancing the efficiency of the electrode system by forming a structure with multiple electrode edges.

Figure 15:
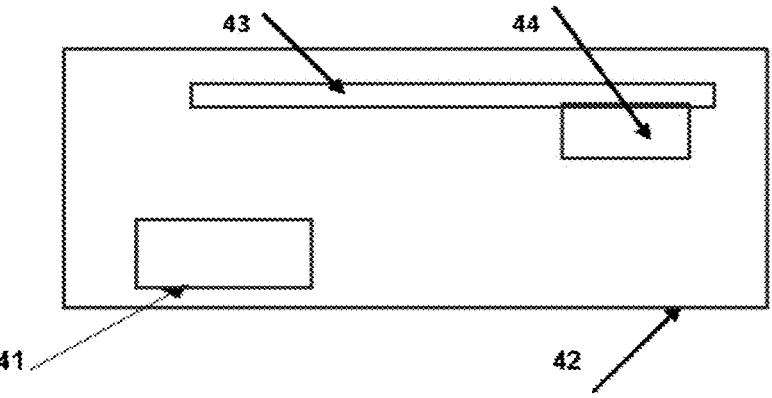
FIG. 15 shows the architecture of the apparatus, according to an exemplary embodiment of the present invention.

FIG. 15 shows a general structure of the portable device including the insulating enclosure 42, the battery 41, the printed circuit board 43 carrying all electronic parts, and the electrode arrangement 44. The right-side wall of the enclosure is the front wall. The right-side edge of the printed circuit board is the front edge. When the device is in action, the front wall of the enclosure is attached to the skin of the subject, such that the wall is in parallel with the tangent of the subject skin. Since the position of the printed circuit board 43 is fixed with respect to the right-side front wall of the enclosure, the positions of the electrodes and electronic parts mounted on the board, as well as the wiring traces of the board are also fixed with respect to the front wall and the subject skin. Particularly, since the front edge of the device PCB is aligned in parallel with the front wall of the device enclosure, the electrodes, wiring traces, and electronic parts are firmly adjusted to the device PCB in a predetermined position e.g. at some predetermined angle and distance with respect to the front edge of the PCB, they are also in a fixed position and distance with respect to the subject skin.

The signal provided by the signal source, such as an oscillator, may have a variety of forms. It may include a series of sinusoidal pulses, rectangular pulses, triangle pulses, exponential form pulses, and/or a steady DC potential. According to the present invention, the signal source may generate AC wave pulses having specific frequencies, such as 8 Hz. This frequency corresponds to Schuman resonance, the effect predicted by Schuman, and later detected as the EM wave frequency generated by the Earth. The semiconducting sphere of the Earth and the ionic Heaviside Layer form a spherical resonance box oscillating at this frequency in response to multiple lightning occurring all the time somewhere on the planet. Even though this pulsation has extremely low power, human beings are subjected to this influence all the time and therefore could be responsive to this frequency. Besides that, 8 Hz is a frequency of the alpha brainwave band (8-12 Hz), associated with a state of wakeful relaxation. Based on this consideration, the 8 Hz wave was chosen as a mild stimulative frequency. 5.37. Another frequency used in the device is 1 Hz. This is a frequency of endogenous pulses driving the heart muscle. Unlike brainwaves with relatively low intensity, 1 Hz is a more powerful pulsation, which may be measured in remote areas of the body, for example on the legs.

Nowadays in many disciplines including acupuncture, reflexology, and acupressure, the active treatment is applied not only to the afflicted area but also to remote zones having some functional features. Experimentation with the application of the EF device shows that using such zones for treatment improves the outcome. Therefore, the described protocols employ similar strategies. There are three types of points:

Local points are the trigger points located in the afflicted area. Usually, they are found by palpation. Examination of the skin includes palpation of an afflicted area and adjacent zones. Using the tip of the thumb or index finger, the practitioner presses each suspected point. As the point is pressed, the patient responds whether any ache, pain, or discomfort is present in the area. Based on the patient's response, the tender points are selected for treatment. Mostly the detected trigger points coincide with acupuncture points known from public sources. Found tender trigger points should be marked for successive treatment.

Distal points are located remotely from the afflicted area and may be effective in the treatment. These points are found in the symmetrical zones of the body, e. g. in the zones on the contralateral side of the body, according to the sagittal symmetry, and on the opposite side of the body, according to the anterior-posterior symmetry. In other words, when the previously found tender point is on the left side of the body, a symmetrical point on the right side of the body should be found, when the previously found tender point is on the front side of the body, the symmetrical point on the back side of the body should be found. Both the original point and its symmetrical counterparts are located at approximately the same height. This method is based on the belt-like shape of dermatomes, representing segmental innervation of the skin. The found points in symmetrical zones should also be palpated, to confirm they are somewhat tender. Most of the trigger points in the symmetrical zones also coincide with some acupuncture points known from public sources. Found tender trigger points should also be marked for successive treatment.

Control points, which are well-known points acquired from acupuncture nomenclature. Three points have been selected for this purpose: ST-36, LI-4, and Sp-6. Stimulation of these points produces specific analgesic, sedative, or homeostatic effects. The preselected control point should also be palpated, to confirm it is somewhat tender. At least one of these points should always be used in the protocol. Description and Location of Control Points Stomach 36 (St-36), or Su San Li in Chinese. It is one of the most powerful points in the body. ST36 is located four finger widths down from the bottom of the kneecap, along the outer boundary of the shin bone. Here is a list of some features associated with the use of this point. It is known as an endurance point because its stimulation raises personal endurance, and when it is needed, energy booster, since it helps mobilize body reserves, in the case of infection it boosts the Immune system, and it is known for its anti-inflammatory features.

Large Intestine 4 (LI-4), He Gu in Chinese. LI4 is located on the dorsum, or the back side of the hand, in the corner between the bones of the first and second fingers. The point may be used for migraines, headaches, various problems manifested on the head and face, anxiety, stress relief, and detoxification.

Spleen 6 (SP6), Sanyinjiao in Chinese. SP6 is located on the medial, or internal side of the leg, four-finger width above the medial, or internal malleolus, or ankle. It may be used to resolve problems of edema and/or swelling in the legs. This point may help cool the body and invigorate circulation. It also helps calm the mind for anxiety and insomnia.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. An electronic apparatus for induction of charges in a skin area of a subject without contacting the skin area, the electronic apparatus comprising:

a signal source; and an electrode system, the electrode system comprising:

reference electrodes operably coupled to the signal source for receiving reference signals; and active electrodes operably coupled to the signal source for receiving active signals, wherein, the reference and the active electrodes form multiple electrode pairs, each electrode pair comprising a single reference electrode and a single active electrode, each electrode pair forming its own electric field, wherein, individual active electrodes may receive different active signals, and accordingly electrode pairs may form different electric fields, wherein an output electric field of the device comprises multiple spatially joined electric fields of different electrode pairs, the output electric field being adapted for application to the skin area, wherein the electrodes receive active signals from the signal source via a signal adjustment circuit, the signal adjustment circuit comprises a voltage divider which comprises capacitors coupled in parallel to an output of the signal adjustment circuit.

2. The electronic apparatus of claim 1, wherein the electrodes are firmly mounted on a top of a device printed circuit board (device PCB), wherein the device PCB is encased within an enclosure such that a surface of the device PCB is perpendicular to an insulating front wall of the enclosure and a front edge of the device PCB is in parallel with the insulating front wall of the enclosure, wherein the insulating front wall of the enclosure is configured to face a target skin area.

3. The electronic apparatus of claim 2, wherein the active electrodes and the reference electrodes comprise conductive plates, conductive wires, conductive wire grids, conductive terminals of electronic parts, or a combination thereof.

4. The electronic apparatus of claim 2, wherein the reference electrodes and the active electrodes comprise conductive plates mounted perpendicularly to the device PCB, wherein edges of each of the reference electrodes and the active electrodes are in parallel to the front edge of the device PCB, wherein the reference electrodes and the active electrodes are mutually coplanar.

5. The electronic apparatus of claim 2, wherein the reference electrodes and the active electrodes comprise conductive plates, and wherein the reference electrodes are not coplanar with the active electrodes.

6. The electronic apparatus of claim 2, wherein the reference electrodes comprise a first reference electrode and a second reference electrode, wherein each of the first and second reference electrodes comprises conducting plates mounted perpendicular to the device PCB and in parallel to the front edge of the device PCB, wherein the first active electrode comprising conductive elements positioned in parallel with the first reference electrode in a non-coplanar way, wherein the conductive elements comprising conductive terminals of electronic parts operably coupled to an active signal output of the signal source.

7. The electronic apparatus of claim 6, wherein the electronic parts are selected from a group consisting of resistors, capacitors, rectifying diodes, Zener diodes, light emitting diodes, integrated circuits, and a combination thereof.

8. The electronic apparatus of claim 6, wherein the conductive elements comprise a wire grid in a form of conductive traces deposited on the top and bottom of the device PCB, wherein the conductive traces being coupled to reference and active outputs of the signal source.

9. The electronic apparatus of claim 1, wherein a signal generated by the signal source has a shape of rectangular pulses with a frequency of 8 Hz.

10. The electronic apparatus of claim 9, wherein the signal generated by the signal source is DC potential measured with respect to a reference potential.

11. The electronic apparatus of claim 2, wherein the active electrode comprises a conductive plate having multiple through-holes, the active electrode is mounted vertically to the device PCB in vicinity of the front edge of the device PCB.

12. The electronic apparatus of claim 2, wherein the active electrodes comprise a first active electrode, and the reference electrodes comprises a first reference electrode, wherein the first active electrode and the first reference electrode comprise conductive plates sandwiching a dielectric layer, wherein the first active electrode, the first reference electrode, and the sandwiched dielectric layer forming an electrode printed circuit board (electrode-PCB), wherein the first reference electrode and the first active electrode are made of double-side copper clad.

13. The electronic apparatus of claim 2, wherein the reference electrodes and the active electrodes are individually positioned at an angle and a distance with respect to the front edge of the device PCB, wherein said angle may have a range from 0 to 90 degrees, wherein the reference electrodes and the active electrodes comprise conductive plates, conductive wires including wiring grids, conductive pins, conductive terminals of electronic parts, or a combination thereof.

14. The electronic apparatus according to claim 1, wherein an active signal generated by the signal source has a shape of rectangular pulses with a frequency of 1 Hz.

15. The electronic apparatus according to claim 8, wherein the conductive traces on one side of the device PCB are coupled to a power supply and the conductive traces on another side of the device PCB are coupled to a reference potential of a power supply, thus together forming a wiring for the power supply of electronic circuits assembled on a top of the device PCB.

16. The electronic apparatus of claim 1, wherein the active signals include the following signals generated simultaneously: rectangular pulses with a frequency of 1 Hz, rectangular pulses with a frequency of 8 Hz, and DC potential measured with respect to the reference potential.

* * * * *